United States Patent [19]

Scott

[11] Patent Number: 5,326,562
[45] Date of Patent: * Jul. 5, 1994

[54] PHARMACEUTICAL DOSAGE UNIT FOR TREATING INFLAMMATION COMPRISING PROTEASE NEXIN-I

[75] Inventor: Randal W. Scott, Cupertino, Calif.

[73] Assignee: Incyte Pharmaceuticals, Inc., Palo Alto, Calif.

[*] Notice: The portion of the term of this patent subsequent to May 12, 2009 has been disclaimed.

[21] Appl. No.: 980,311

[22] Filed: Nov. 23, 1992

Related U.S. Application Data

[60] Division of Ser. No. 804,332, Dec. 6, 1991, Pat. No. 5,206,017, which is a continuation-in-part of Ser. No. 505,442, Apr. 5, 1990, Pat. No. 5,112,608, which is a continuation-in-part of Ser. No. 25,450, Mar. 13, 1987, Pat. No. 5,278,049, which is a continuation-in-part of Ser. No. 871,501, Jun. 6, 1986, abandoned, which is a continuation-in-part of Ser. No. 870,232, Jun. 3, 1986, abandoned.

[51] Int. Cl.5 ............ A61K 37/547; A61K 37/48; A61K 37/54
[52] U.S. Cl. ................. 424/94.64; 424/94.1; 424/94.63; 424/94.6
[58] Field of Search ............ 424/94.1, 94.64, 94.63, 424/94.6, 443, 434, 400

[56] References Cited

U.S. PATENT DOCUMENTS 5,006,252  4/1991  Scott et al. ............ 210/635
5,112,608  5/1992  Scott et al. ............ 424/94.64

FOREIGN PATENT DOCUMENTS 0233838  8/1987  European Pat. Off. .

OTHER PUBLICATIONS

McGuire-Goldring et al., Arthritis & Rheumatism, p. S24, abstract #51 (1984).
Baker et al., J. of Cellular Physiology, vol. 112, (1982), pp. 291-297.
Conn, P. (ed), The Receptors, vol. III, published by Academic Press Inc., "Protease Nexins: Secreted Protease Inhibitors that Regulate Protease Activity at or Near the Cell Surface," chapter 5, pp. 153-172 (1986).

*Primary Examiner*—Douglas W. Robinson
*Assistant Examiner*—Susan M. Dadio
*Attorney, Agent, or Firm*—Karl Bozicevic

[57] ABSTRACT

Methods and pharmaceutical compositions for treatment of inflammation and arthritis using protease nexin-I as an active ingredient are disclosed.

12 Claims, No Drawings

PHARMACEUTICAL DOSAGE UNIT FOR TREATING INFLAMMATION COMPRISING PROTEASE NEXIN-I

CROSS REFERENCES

This application is a divisional of copending U.S. application Ser. No. 07/804,332 filed Dec. 6, 1991, now U.S. Pat. No. 5,206,017, which is a continuation-in-part of U.S. application Ser. No. 07/505,442 filed Apr. 5, 1990, now U.S. Pat. No. 5,112,608, which is a continuation-in-part of U.S. application Ser. No. 07/025,450 filed Mar. 13, 1987, now U.S. Pat. No. 5,278,049l, which is a continuation-in-part of U.S. application Ser. No. 06/871,501 filed Jun. 6, 1986, now abandoned, which is a continuation-in-part of U.S. application Ser. No. 06/870,232 filed Jun. 3, 1986, now abandoned, all of which are incorporated herein by reference and to which applications we claim priority under 35 USC § 120.

TECHNICAL FIELD

The invention relates to the field of treatment of conditions characterized by inflammation or inflammatory responses. More specifically, it concerns treatment of inflammation and inflammatory diseases with protease nexin-1.

BACKGROUND ART

The structure and recombinant production of protease nexin-I are described in European patent application 251505, published Jan. 7, 1988, and incorporated herein by reference. The contents of this publication are substantially the same as those of above-referenced Ser. No. 07/025,450, which case is allowed and involved in an interference. As disclosed in these documents, protease nexin-I occurs naturally in two closely related forms, PN-Iα and PN-Iβ, which result from alternate splicing events in the mRNA message encoding the protein. PN-Iα and PN-Iβ consist of 378 and 379 amino acids, respectively, and differ only in that the arginyl residue at position 310 of PN-Iα is replaced by a thr-gly sequence in PN-Iβ. PN-Iα and PN-Iβ can be prepared individually using recombinant means or the natively produced protein can be isolated from various tissue sources such as human fibroblasts or glial cells. Methods for purifying protease nexin-I to apparent homogeneity from fibroblasts have been described by Scott, R. W., et al., *J. Biol Chem* (1985) 260:7029-7034.

The ability of protease nexin-I to inhibit various anti-clotting factors such as urokinase and tissue plasminogen activator is well established. It is also known that protease nexin-I stimulates the growth of neurites. It has now been demonstrated that protease nexin-I is effective in preventing degradation of connective tissue and in the treatment of inflammatory diseases such as arthritis.

DISCLOSURE OF THE INVENTION

The invention is directed to pharmaceutical compositions and methods useful in the treatment of inflammation and arthritis. The compositions may contain either PN-Iα or PN-Iβ or both, and may contain additional active ingredients as well as standard excipients. The methods of treatment involve administration of the foregoing compositions in suitable protocols for the control of these conditions. Local administration to the site of inflammation is particularly preferred.

MODES OF CARRYING OUT THE INVENTION

The conditions for which treatment with protease nexin-I is indicated include inflammation and arthritis, in particular, acute or chronic inflammation, acute or chronic arthritis. Particular conditions that may benefit from administration of the compounds of the invention include osteoarthritis, rheumatoid arthritis, degenerative arthritis, psoriatic arthritis (psoriasis), pemphigus, joint inflammation, conditions treated by collagen therapy, juvenile arthritis, ankylosing spondylitis, inflammatory bowel disease, sepsis, emphysema, adult respiratory distress syndrome (ARDS) and septic joints.

Inflammation may occur from a variety of causes and is evidenced by swelling and reddening at the inflamed location or can comprise an overall physiological response characterized by pain and fever. Depending on the nature of the condition, either systemic or local administration of protease nexin-1 compositions is employed. A preferred means of administration is by injection; suitable dosage ranges are of the order of 0.1–1000 mg per injection daily, preferably 1–10 mg per injection daily. For injection, the protease nexin is formulated into a liquid formulation or a solid which can be reconstituted as a suspension or solution. Suitable excipients for use in injection include physiological saline, Hank's solution, Ringer's solution, and the like. Additional excipients such as stabilizers, buffers, solubilizing agents and the like can also be included. Suitable modes for injection include intravenous, intramuscular, subcutaneous, peritoneal and, as described herein, localized treatment. The protocol may involve a single injection or multiple doses at spaced intervals. Multiple doses may be identical in level or may differ according to design optimization parameters which can be routinely determined. Similar protocols are useful in treating arthritic subjects although the treatment in these cases is more likely to extend over prolonged periods due to the chronic nature of this condition.

For inflammation focused at particular locations, localized administration at the site is preferred. It is desirable to obtain levels at the inflammation site of 10–100 μg/ml PN-I.

Suitable routes of systemic administration, besides injection, also include transdermal, transmucosal, or oral administration.

Transmucosal administration takes advantage of the ability of certain excipients to cause the active ingredient protease nexin-I to cross mucosal barriers. Transmucosal administration generally requires less disruption of tissue than does transdermal administration which is known to require specialized effectors. Suitable materials to effect the transmucosal passage of protease nexin-I include certain steroids such as bile salts and fusidic acid derivatives, as well as additional detergents such as laurates or aromatic sulfonates. Transmucosal administration may be by, for example, aerosol delivery to the nasal passages, by suppository, or transbuccal dosages. Transdermal administration is more difficult, and generally through skin patches such as those placed behind the ear or in other skin areas which are relatively unresistant to the passage of materials.

Oral administration is also difficult, but not impossible when the compounds are properly formulated to prevent their degradation in the digestive tract. Various enteric compositions are known which may assure the passage of the protease nexin-I into the blood stream without degradation in the stomach.

All of the foregoing may be adapted to provide PN-I localized to the site of inflammation in the case of, for example, inflamed joints, local trauma, or digestive tract inflammation.

Preferably, the protease nexin-I is provided in unit dosage form for easy administration in the devised protocol.

The following examples are intended to illustrate but not to limit the invention.

EXAMPLE 1

Inhibition of Glycosaminoglycan (GAG) Loss by PN-I

A model for arthritis in rabbits is constructed as follows: the right knee of anesthetized Pasteurella-free New Zealand white rabbits was injected with a single dose of either recombinant human IL-1 (Amgen, specific activity $5 \times 10^8$ U/mg) and recombinant human serine analog bFGF (Fox, G. M., et al., *J Biol Chem* (1988) 263:18452–18458) alone or in combination. The left knee was injected with an equal volume of vehicle as a contralateral control. At various times after injection, the rabbits were euthanized, and each knee joint was rinsed with 1 ml saline. The fluid was assayed for cell infiltration by microscopic examination and for glycosaminoglycan (GAG) content by the assay of Farndale, R. W., et al., *Biochem Biophys Acta* (1986) 883:173–177. The knees were removed, the cartilage scraped from the tibial plateau, and the cartilage digested overnight at 65° C. with papain. The GAG is reported as µg/mg by weight of cartilage.

In this assay, various doses of PN-I or vehicle were given intraarticularly to the right knees for four days, one day before induction of arthritic conditions by IL-1/FGF, and then daily for three additional days. The inducing dosages of bFGF and IL-1 were 10 µg and 10,000 units, respectively.

In a series of controlled experiments, treatment with PN-I consistently showed prevention of GAG loss as compared to control.

In one series of experiments, PN-I treatment at 2.5 mg/day resulted in only a 19% GAG loss as compared to 31% loss of GAG in the control (p=0.05).

In a second series of experiments, PN-I treatment at 2 mg/day resulted in only a 23% loss in GAG as compared to 45% in the control (p<0.001). In a third protocol, dosages of 0.5 rag/day and 1 mg/day resulted in 37% and 38% losses, respectively, as compared to 41% loss of GAG in the control. Thus, PN-I consistently reversed the arthritic effect of the bFGF/IL-1 stimulation. Administration of 2.5 mg cytochrome c had no effect.

I claim:

1. A pharmaceutically acceptable injectable dosage unit for treating inflammation, comprising:
    a pharmaceutically effective amount of protease nexin-I; and
    a pharmaceutically acceptable carrier.

2. The dosage unit of claim 1, wherein protease nexin-I is present in an amount sufficient to reduce the loss of glycosaminoglycans from connective tissue and thereby reduce inflammation.

3. The dosage unit of claim 1, wherein the protease nexin-I is present in an amount in the range of from 0.1 to 1,000 mg.

4. The dosage unit of claim 1, wherein the protease nexin-I is present in an amount in the range of 1 to 10 mg.

5. The dosage unit of claim 1, wherein the carrier is in the form of a physiological saline solution.

6. A pharmaceutically acceptable, injectable dosage unit for treating inflammation, comprising:
    a pharmaceutically effective amount of protease nexin-I in the range of from about 1 to 10 mg; and
    a pharmaceutically acceptable carrier in the form of a physiological saline solution.

7. The dosage unit of claim 6, wherein protease nexin-I is present in an amount sufficient to reduce the loss of glycosaminoglycans from connective tissue and thereby reduce inflammation.

8. A pharmaceutically acceptable, transmucosal dosage unit for treating inflammation, comprising:
    an amount of protease nexin-I sufficient to reduce the loss of glycosaminoglycans from connective tissue and thereby reduce inflammation; and
    a pharmaceutically acceptable carrier comprising a bile salt, a fusidic acid derivative, and a detergent.

9. A pharmaceutically acceptable, transbuccal dosage unit for treating inflammation, comprising:
    an amount of protease nexin-I sufficient to reduce the loss of glycosaminoglycans from connective tissues and thereby reduce inflammation; and
    a pharmaceutically acceptable carrier combined with the protease nexin-I in a manner so as to form the transbuccal dosage unit.

10. A pharmaceutically acceptable, transdermal dosage unit for treating inflammation, comprising:
    an amount of protease nexin-I sufficient to reduce the loss of glycosaminoglycans from connective tissue and thereby reduce inflammation; and
    a pharmaceutically acceptable carrier.

11. A pharmaceutically acceptable, oral dosage unit for treating inflammation, comprising:
    an amount of protease nexin-I sufficient to reduce the loss of glycosaminoglycans from connective tissue and thereby reduce inflammation; and
    a pharmaceutically acceptable carrier in the form of an enteric composition which prevents the protease nexin-I from being degraded in the digestive tract.

12. A pharmaceutically acceptable, aerosol dosage unit for treating inflammation, comprising:
    an amount of protease nexin-I sufficient to reduce the loss of glycosaminoglycans from connective tissue and thereby reduce inflammation; and
    pharmaceutically acceptable carrier.

* * * * *